United States Patent [19]

Peterson et al.

[11] 4,173,463

[45] Nov. 6, 1979

[54] PHOSPHONIUM SALTS AS HERBICIDES

[75] Inventors: Larry W. Peterson, Oakdale; Gene A. Bozarth; Kurt H. G. Pilgram, both of Modesto, all of Calif.

[73] Assignee: Shell Oil Company, Houston, Tex.

[21] Appl. No.: 956,457

[22] Filed: Oct. 31, 1978

[51] Int. Cl.$^2$ ............................................. A01N 9/36
[52] U.S. Cl. .......................................... 71/87; 71/86
[58] Field of Search ................................... 71/87, 86

[56] References Cited

U.S. PATENT DOCUMENTS

| | | | |
|---|---|---|---|
| 2,745,877 | 5/1956 | Bindler et al. | 260/606.5 F |
| 3,050,543 | 8/1962 | Melton | 71/87 |
| 3,103,431 | 9/1963 | Wilson, Jr. | 71/78 |
| 3,230,069 | 1/1966 | Preston, Jr. | 71/86 |
| 3,502,731 | 3/1970 | Peterson | 71/87 |
| 3,755,510 | 8/1973 | Chan | 71/86 |

OTHER PUBLICATIONS

Wittig et al., Chem. Berichte, vol. 94, (1961). 1373-1383.

Primary Examiner—Catherine L. Mills

[57] ABSTRACT

Use as herbicides of certain phosphonium salts of the formula

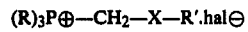

$(R)_3P^\oplus—CH_2—X—R'.hal^\ominus$ wherein the symbols have defined meanings.

1 Claim, No Drawings

PHOSPHONIUM SALTS AS HERBICIDES

DESCRIPTION OF THE INVENTION

It has been found that valuable herbicidal properties are possessed by phosphonium compounds of the formula

$$(R)_3P^{\oplus}-CH_2-X-R'.hal^{\ominus} \quad (I)$$

wherein R is naphthyl, or is phenyl or phenalkyl optionally substituted by from one to three moieties selected from alkyl of from 1 to 6 carbon atoms, middle halogen, nitro, amino, and trifluoromethyl, and when R is phenalkyl it contains from 1 to 4 carbon atoms in the linking alkyl moiety, with from 1 to 2 carbon atoms linking the phenyl moiety to the phosphorus atom; or is alkyl of from 1 to 12 carbon atoms, or cycloalkyl of from 5 to 6 carbon atoms; X is —O—, —S—, —SO— or —SO$_2$—; R' is alkyl of from 1 to 4 carbon atoms, alkenyl of from 3 to 5 carbon atoms, or is phenyl or substituted phenyl as defined for R; hal is chlorine, bromine or iodine.

In these compounds, each alkyl moiety suitably is either straight-chain or branched-chain in configuration. By "middle halogen" is meant bromine and chlorine.

Typical, exemplary individual species of this class of compounds, the manner in which they can be prepared, and summaries of their herbicidal properties, are set forth in the examples hereinafter. Other, typical, individual species are the following (in which the symbols refer to Formula I):

| R | X | R' | hal |
|---|---|----|----|
| phenyl | —O— | methyl | Cl |
| benzyl | —S— | methyl | Cl |
| benzyl | —S— | methyl | Cl |
| benzyl | —S— | 4-chlorophenyl | Cl |
| benzyl | —O— | methyl | Cl |
| benzyl | —O— | ethyl | Cl |
| 4-methoxyphenyl | —S— | methyl | Cl |
| 4-methoxyphenyl | —S— | 4-chlorophenyl | Cl |
| 4-methoxyphenyl | —O— | methyl | Cl |
| 4-methoxyphenyl | —O— | ethyl | Cl |
| 3-chlorophenyl | —S— | methyl | Cl |
| 3-chlorophenyl | —S— | 4-chlorophenyl | Cl |
| 3-chlorophenyl | —O— | methyl | Cl |
| 3-chlorophenyl | —O— | ethyl | Cl |
| 4-fluorophenyl | —S— | methyl | Cl |
| 4-fluorophenyl | —S— | 4-chlorophenyl | Cl |
| 4-fluorophenyl | —O— | methyl | Cl |
| 4-fluorophenyl | —O— | ethyl | Cl |
| ethyl | —S— | methyl | Cl |
| ethyl | —S— | 4-chlorophenyl | Cl |
| ethyl | —O— | methyl | Cl |
| ethyl | —O— | ethyl | Cl |
| n-octyl | —S— | methyl | Cl |
| n-octyl | —S— | 4-chlorophenyl | Cl |
| n-octyl | —O— | methyl | Cl |
| n-octyl | —O— | ethyl | Cl |
| n-butyl | —SO— | 4-chlorophenyl | Cl |
| phenyl | —SO— | ethyl | Cl |
| butyl | —S— | 2,4-dichlorophenyl | Cl |
| butyl | —O— | 2,4-dichlorophenyl | Cl |
| butyl | —O— | 4-chlorophenyl | Cl |
| cyclohexyl | —S— | methyl | Cl |

Compounds of Formula I wherein hal is chlorine or bromine and X is —O— or —S— can be prepared by reacting a phosphine, (R)$_3$P, with a chloro- or bromomethyl ether, or thioether, Cl(Br)—CH$_2$X—R'. The reaction is conducted by mixing the two reactants in a solvent, such as p-dioxane, benzene or xylene, at a moderately elevated temperature—for example, 80°–150° C. This method is described by H. Sasse in "Methoden Der Organischen Chemie" (Houben-Weyl), vol. 12/1, p 79 (1963).

Compounds of Formula I wherein X is —SO— or —SO$_2$— can be prepared by oxidation of compounds of Formula I wherein X is —S—. The oxidation can be carried out in a solvent such as chloroform or methylene chloride, using meta-chloroperbenzoic acid as oxidant, at a temperature of from about 10°–40° C. Other suitable oxidizing agents include ferric chloride, chromic acid, potassium permanganate, hydrogen peroxide, or other oxidizing agent commonly used to oxidize sulfides to sulfoxides or sulfones. Use of one molar equivalent of the oxidant tends to effect oxidation to the sulfoxide, whereas use of two molar equivalents tends to form the sulfone. The method is described by A. Schoberl in Houben-Weyl, supra, vol. 9, p 227 (1955).

Conversion of the chloride or the bromide to the iodide can be affected by treating the chloride or bromide with methyl iodide in acetone at an elevated temperature—for example, 100° C.—in a closed container. The method is described in the article by Sasse, supra, at page 104.

The preparation of typical individual species of compounds of Formula I are shown in the following examples. In each case, the identity of the product was confirmed by appropriate chemical and spectral analyses.

EXAMPLE 1

Tributyl((4-chlorophenylthio)methyl)phosphonium chloride (1)

A solution of 8.45 g of tri(n-butyl)phosphine and 8.33 g of chloromethyl 4-chlorophenyl sulfide in 25 ml of p-dioxane was stirred and refluxed (101°–102° C.) for 20 hours. The mixture was cooled to room temperature and diluted with 100 ml of hexane. The white precipitate was filtered and dried to give 1, as a solid, mp 113°–114° C.

EXAMPLES 2–4

By the procedure described in Example 1, there were prepared:

tributyl((methylthio)methyl)phosphonium chloride (2), as a solid, mp 91°–93° C.;

((methylthio)methyl)triphenylphosphonium chloride (3), as a solid, mp 215°–216° C.;

((4-chlorophenylthio)methyl)triphenylphosphonium chloride (4), as a solid, mp 230°–232° C.

EXAMPLE 5

((Methylsulfonyl)methyl)triphenylphosphonium chloride (5)

A saturated solution of 6.08 g of 85% meta-chloroperbenzoic acid in chloroform was added to a solution of 5.0 g of 3 in the minimum amount of chloroform. The mixture was held at room temperature for 72 hours, then the solvent was evaporated. The residue was extracted repeatedly with ether to remove meta-chlorobenzoic acid and excess m-chloroperbenzoic acid. The residue was dissolved in the minimum amount of ethanol. To the resulting solution was added an equal volume of tetrahydrofuran, followed by five volumes of hexane. The precipitate was filtered and dried to give 5, as an off-white solid, mp 166°–167° C. (with decomposition).

EXAMPLE 6

By the procedure described in Example 5, ((4-chlorophenylsulfonyl)methyl)triphenylphosphonium chloride (6) was prepared, as a solid, mp 198°-200° C.

EXAMPLE 7

(Ethoxymethyl)triphenylphosphonium chloride (7)

A solution of 99.66 g of triphenylphosphine and 37.82 g of chloromethyl ethyl ether in 240 ml of dry benzene was stirred and refluxed (84° C.) for 6 hours. The mixture then was chilled and filtered to give 7, as a white solid, mp 205°-206° C.

EXAMPLE 8

By the procedure described in Example 7, tributyl(ethoxymethyl)phosphonium chloride (8) was prepared as a solid, mp 60°-62° C.

EXAMPLE 9

((Methylthio)methyl)triphenylphosphonium chloride (9)

A sealed glass cylinder containing a solution of 10 g of 3 in 70 ml of methyl iodide and 5 ml of acetone was heated for 7 hours on a steam bath (95°-100° C.). The mixture then was cooled and filtered. The solid product was washed with ether and dried to give 9, as a pale yellow solid, mp 203°-205° C.

EXAMPLE 10

By the procedure described in Example 9, tributyl((methylthio)methyl)phosphonium iodide was prepared as a solid, mp 61°-63° C., from 2.

Compounds of Formula I have been found to be useful for controlling growth of unwanted plants. They have been found to be particularly effective when applied post-emergence—that is, to the foliage of the growing plant.

Accordingly, the invention includes a method of controlling plant growth which comprises applying to the foliage an effective amount of a compound of Formula I. Likewise, the invention also includes plant growth regulating compositions comprising a carrier or a surface-active agent, or both a carrier and a surface-active agent, and, as active ingredient, at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example natural silicas such as diatomaceous earths; magnesium silicates, for example, attapulgites and vermiculities; aluminum silicates, for example, kaolinites, montmorilloinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Examples of suitable fluid carries are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3-10% by weight of a dispersing agent, 1-5% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½-10% by weight of toxicant. Granules are usually prepared to have a size between 10 and 100 BS mesh (1.676-0.152 mm), and may be manufactured by agglomeration or impregnation techniques. Generally granules will contain ½-25% by weight toxicant and 0-10% by weight of additives such as stabilizers, slow release modifiers and binding agents. Emulsifiable concentrates usually contain, in addition to the solvent and, when necessary, cosolvent, 10-50% weight per volume toxicant, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% w toxicant, 0.5-5% w of dispersing agents, 1-5% of surface-active agent, 0.1-10% w of suspending agents such as protective colloids and thixotropic agents, 0-10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable plant growth. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound used in this invention will be satisfactory.

EXAMPLES OF HERBICIDAL ACTIVITY

The pre-emergence herbicidal activity of compounds of the invention was evaluated by planting seeds of watergrass, garden cress, downy brome, sicklepod, velvetleaf, and yellow foxtail in test tubes, nominally measuring 25×200 millimeters, containing soil treated with the test compound at the rates of 0.1 and 1 milligram per tube, respectively. The planted soil was held under controlled conditions of temperature, moisture, and light for 9 to 10 days. The amount of germination and growth in each tube were evaluated on a 0 to 9 scale, 0 rating indicating no effect, 9 death of the seedlings or no germination.

All of compounds 1–10 were found to have little or no effect when applied pre-emergence.

The post-emergence activity of the compounds of this invention was evaluated by spraying 10-day old crabgrass plants, 13-day old pigweed plants, 6-day old downy brome plants, 9-day old sicklepod plants, 9-day old velvetleaf plants and 9-day old yellow foxtail plants to runoff with a liquid formulation of the test compound at the rates of 2.4 milliliters of a 0.025% solution designated Rate I in Table I, and 2.4 milliliters of a 0.25% solution designated Rate II in Table I. The sprayed plants were held under controlled conditions for 7 to 8 days and the effect of the test compound was then evaluated visually, the results being rated on the 0 to 9 scale described above.

The results of the tests are summarized in Table I.

TABLE I

| Compound | Crabgrass I | II | Pigweed I | II | Downy Brome I | II | Sicklepod I | II | Velvetleaf I | II | Yellow Foxtail I | II |
|---|---|---|---|---|---|---|---|---|---|---|---|---|
| 1 | — | 8 | — | 9 | 2 | 6 | 5 | 9 | 4 | 9 | 2 | 5 |
| 2 | 6 | 7 | 5 | 9 | 4 | 5 | 1 | 8 | 3 | 8 | 0 | 2 |
| 3 | 2 | 6 | 2 | 9 | 2 | 4 | 5 | 9 | 3 | 9 | 2 | 6 |
| 4 | 0 | 5 | 1 | 7 | 0 | 5 | 1 | 8 | 7 | 9 | 0 | 5 |
| 5 | 0 | 2 | 2 | 7 | 1 | 3 | 2 | 6 | 2 | 4 | 2 | 3 |
| 6 | 2 | 8 | 4 | 9 | 0 | 3 | 3 | 8 | 3 | 9 | 2 | 9 |
| 7 | 0 | 6 | 4 | 8 | 2 | 5 | 6 | 8 | 7 | 8 | 2 | 4 |
| 8 | 2 | 4 | 1 | 7 | 0 | 5 | 5 | 9 | 2 | 7 | 1 | 6 |
| 9 | 3 | 5 | 2 | 8 | 2 | 4 | 7 | 8 | 2 | 7 | 2 | 7 |
| 10 | 2 | 3 | 2 | 7 | 2 | 3 | 3 | 8 | 3 | 9 | 3 | 5 |

The herbicidal activity of three individual species of the compounds of this invention was further determined with respect to several common species of weeds, by spraying a formulation of the test compound onto the foliage of the plants (post-emergence test). In each series of tests, the plants were grown in narrow trays and sprayed with chemical. The solution of the test compound was sprayed over the tray, from one end to the other, the concentration of the test compound in the formulation varying logarithmically from a higher value at one end of the band to a lower value at the other end of the band. The effect of the test compound was evaluated visually and reported as the nominal rate of application, in pounds of test compound per acre of the soil band, at which 90% inhibition of the growth of the weeds occurred, this being referred to as the 90% growth inhibition, of $GI_{90}$, dosage. Results of the tests, as well as the weed species involved, are set out in Table II.

TABLE II

| | $GI_{90}$ | | | | | | | |
|---|---|---|---|---|---|---|---|---|
| Compound No. | Yellow Foxtail | Prickly sida | Crabgrass | Pigweed | Wild Mustard | Velvetleaf | Downy Brome | Barnyard grass |
| 1 | 3.7 | 0.8 | >5 | 1.7 | 2.1 | 2.3 | >5 | — |
| 3 | 4.5 | 1.9 | >5 | 0.55 | 1.3 | 2.5 | >5 | >5 |
| 7 | >5 | 0.9 | >5 | 2.8 | 1.0 | 2.3 | >5 | — |

(The symbol > means "greater than".)

The herbicidal effectiveness of two individual species of the compounds of the invention also was ascertained by spraying a formulation of the test compound on the leaves of growing plants, and in due course visually evaluating its effect on the plants, the results also being rated on the 0 to 9 scale described above. Each test compound was applied at two rates: 2 and 4 pounds per acre. The results are summarized in Table III.

TABLE III

RATING OF INDICATED TEST COMPOUND AT INDICATED DOSAGE FOR INDICATED PLANT SPECIES

| Plant Species | Compound 3 | | Compound 7 | |
|---|---|---|---|---|
| | 4#/A | 2#/A | 4#/A | 2#/A |
| Corn | 5 | 2 | 0 | 0 |
| Cotton | 7 | 6 | 7 | 7 |
| Rice | 0 | 0 | 0 | 0 |
| Sorghum | 4 | 2 | 0 | 0 |
| Soybean | 6 | 4 | 6 | 4 |
| Wheat | 2 | 0 | 4 | 3 |
| Barnyard grass | 2 | 0 | 3 | 2 |
| Crabgrass | 3 | 2 | 3 | 0 |
| Downy brome | 2 | 0 | 3 | 2 |
| Giant Foxtail | 8 | 3 | 0 | 0 |
| Wild Oats | 3 | 0 | 0 | 0 |
| Yellow Foxtail | 3 | 0 | 5 | 0 |
| Coffeeweed | 8 | 8 | 8 | 7 |
| Jimsonweed | 9 | 9 | 9 | 9 |
| Morning glory | 8 | 5 | 9 | 6 |
| Wild mustard | 9 | 5 | 9 | 7 |
| Pigweed | 9 | 6 | 7 | 9 |
| Prickly sida | 8 | 6 | 9 | 4 |
| Sicklepod | 9 | 9 | 9 | 7 |
| Velvet leaf | 6 | 6 | 7 | 7 |

We claim:

1. A method for controlling unwanted plant growth which comprises applying to the foliage of the unwanted plant an effective dosage of a compound of the formula $$(R)_3P^\oplus-CH_2-X-R' \cdot hal^\ominus \qquad (I)$$

wherein R is naphthyl, or is phenyl or phenalkyl optionally substituted by from one to three moieties selected from alkyl of from 1 to 6 carbon atoms, middle halogen, nitro, amino, and trifluoromethyl, and when R is phenalkyl it contains from 1 to 4 carbon atoms in the linking alkyl moiety, with from 1 to 2 carbon atoms linking the phenyl moiety to the phosphorus atom; or is alkyl of from 1 to 12 carbon atoms, or cycloalkyl of from 5 to 6 carbon atoms; X is —O—, —S—, —SO— or $SO_2$—; R' is alkyl of from 1 to 4 carbon atoms, alkenyl of from 3 to 5 carbon atoms, or is phenyl or substituted phenyl as defined for R; hal is chlorine, bromine or iodine.

* * * * *